(12) United States Patent
Cohen et al.

(10) Patent No.: US 6,710,026 B1
(45) Date of Patent: Mar. 23, 2004

(54) PROTEIN DOMAINS IN THE HEPATIC GLYCOGEN-TARGETTING SUBUNIT OF PROTEIN PHOSPHATASE 1 AND METHODS OF MAKING AND USING THE SAME

(75) Inventors: Patricia Townsend Wade Cohen, Invergowrie (GB); Christopher George Armstrong, Dundee (GB); Martin John Doherty, Edinburgh (GB)

(73) Assignee: Medical Research Counsel (GB)

( * ) Notice: Subject to any disclaimer, the term of this patent is extended or adjusted under 35 U.S.C. 154(b) by 0 days.

(21) Appl. No.: 09/763,848

(22) PCT Filed: Aug. 19, 1999

(86) PCT No.: PCT/GB99/02761

§ 371 (c)(1),
(2), (4) Date: Sep. 26, 2001

(87) PCT Pub. No.: WO00/12549

PCT Pub. Date: Mar. 9, 2000

(30) Foreign Application Priority Data

Aug. 27, 1998 (GB) .............................................. 9818650

(51) Int. Cl.⁷ .......................... A61K 38/00; C07K 7/00; G01N 33/00
(52) U.S. Cl. .............................. 514/2; 436/86; 530/300
(58) Field of Search ................................ 514/12, 2, 13; 436/86; 530/300, 326

(56) References Cited

FOREIGN PATENT DOCUMENTS

EP           0 846 763      6/1998
WO    PCT WO 97/37224    10/1997

OTHER PUBLICATIONS

Alemany & Cohen, FEBS Lett 198:194–202 (1986).
Armstrong et al., FEBS Lett 418:210–214 (1997).
Armstrong et al., Biochemical J 336:699–704 (1998).
Bollen & Stalmans, Crit Rev Biochem Mol Biol 27:227–281 (1992).
Brady et al., J Biol Chem 272:20198–20204 (1997).
Chen et al., Diabetes 43:1234–1241 (1994).
Cohen et al., Curr Topic Cell Regul 14:117–196 (1978).
Cohen et al., Meth Enzymol 159:390–408 (1988).
Doherty et al., FEBS Lett 375:294–298 (1995).
Doherty et al., FEBS Lett 399:339–343 (1996).
Dubois et al., Anal Chem 28:350–356 (1956).
Egloff et al., EMBO J 16:1876–1887 (1997).
Francois et al., EMBO J 11:87–96 (1992).
Goldsmith et al., J Mol Biol 156:411–427 (1982).
Hubbard & Cohen, Trends Biochem Sci 18:172–177 (1993).
Johnson et al., Curr Topics Microbiol & Immunol 139:81–134 (1988).
Johnson et al., Eur J Biochem 239:317–325 (1996).
MacKintosh et al., FEBS Lett 371:236–240 (1995).
Martin et al., Biochemistry 30:10101–10116 (1991).
Martin et al., PNAS U.S.A. 95:1776–1781 (1998).
Moorhead et al., FEBS Lett 362:101–105 (1995).
Nakano et al., FEBS Lett 204:283–287 (1986).
Printen et al., Science 275:1475–1478 (1997).
Tanaka et al., Agric Biol Chem 50:965–969 (1986).
Tang et al., J Biol Chem 266:15782–15789 (1991).
Zhao & Lee J Biol Chem 272:28368–28372 (1997).

*Primary Examiner*—Nashaat T. Nashed
(74) *Attorney, Agent, or Firm*—Rogalsky, I Weyand, LLP (57) ABSTRACT

The present invention relates to compounds useful for treating disorders associated with abnormal blood glucose levels in mammals, such as Type I and Type II diabetes. The invention also relates to methods of making and using such compounds.

12 Claims, 7 Drawing Sheets

$M_{110}$ (1-38)peptide    26    ...PPVV<u>KRQK</u>TKVKF    38

$G_L$    52    ...TVQE<u>KKVKKR</u>VSFADQGL...    69

$G_M$ (63-93)peptide    63    G<u>RR</u>VSFADNFG...    73

*Fig. 5*

```
G_L    132  VCLE---NCVLKEKAIAGTVKVQNLAFEKVVKIRM--TFDTWKSFT      172
R5     157  VCLE---NCSLQERTVTGTVKVKNVSFEKKVQIRI--TFDSWKNYT      197
R6     177  VCLE---RVTCSDLGISGTVRVCNVAFEKQVAVRY--TFSGWRSTH      217
G_M    128  AILES-TESLLGSTSIKGIIRVLNVSFEKLVYVRM--SLDDWQTHY      170
GAC1   244  VKLHSLTQLGDDSSKITGLVYVKNLSFEKYLEIKF--TFNSWRDIH      287
AMYL    33  VQLDS---YNYDGSTFSGKIYVKNIAYSKKVTVIYADGSDNWNNG       75
Consensus        φ.G.V.V.Nφ.F.K.V.V.φ.....W
                   I       Y  L I
PHOS   398              RHLQIIYEINQRFLNRVAAAFPGDVDRLRRMS      429
                        ** ***                      *
```

```
G_L    173  DFPCQYVKDTYAGSDRDTFSFDISLPEKIQSYE-------------      205
R5     198  DVDCVYMKNVYGGTDSDTFSFAIDLPPVIPTEQ-------------      230
R6     218  EAVARWRGPAGPEGTEDVFTFGFPVPPFLLELGS------------      251
G_M    171  DILAEYVPNSCDG-ETDQFSFKIVLVPPYQKDGS------------      203
GAC1   288  YVTANFNRTIN--SNVDEFKFTIDLNSLKYILLIKRIITMEKNTSS      331
AMYL    76  NTIAASYSAPISGSNYEYWTFSASINGIK-----------------      104
Consensus                  D.F.F...φ
                           E W
PHOS   330  LVEEGAVK                                             437
            *  *   *
```

```
G_L    206  ---RMEFAVCYECNGQSYWDSNKGKNYRI                        231
R5     231  ---KIEFCISYHANGQVFWDNNDGQNYRI                        256
R6     252  ---RVHFAVRYQVAGAEYWDNNDHRDYSL                        282
G_M    204  ---KVEFCIRYETSVGTFWSNNNGTNYTF                        229
GAC1   332  CPLNIELCCRYDVNNETYYDNNNGKNYHL                        360
AMYL   105  -----EFYIKYEVSKGTYYDNNNSANYQV                        128
Consensus        F.φ.Y......YW..N....Y.φ
                 L              FY
```

PROTEIN DOMAINS IN THE HEPATIC GLYCOGEN-TARGETTING SUBUNIT OF PROTEIN PHOSPHATASE 1 AND METHODS OF MAKING AND USING THE SAME

The present invention relates to compounds useful in the treatment of disorders associated with abnormal blood glucose levels, particularly in the prevention of phosphorylase-a binding to the glycogen targeting subunit ($G_L$) of protein phosphatase 1 (PP1). Such compounds are useful for increasing glycogen synthesis and thereby reducing blood glucose levels. The compounds find utility in the treatment of disorders, such as type I and type II diabetes, associated with higher than normal levels of blood glucose (hyperglycaemia).

Most of the adverse physiological consequences in type I and type II diabetes arise from the higher than normal levels of blood glucose. Although high blood glucose levels can be reduced by administration of insulin in type I diabetes and by dietary restrictions in the case of type II diabetes, a drug which aids reduction of blood glucose levels would be advantageous in the treatment of these disorders. The liver, which is the main organ regulating glucose homeostasis, is able to store glucose in the form of glycogen and the synthesis of hepatic glycogen from glucose is under the control of hepatic glycogen synthase.

Protein phosphatase 1 is major protein serine/threonine phosphatase in eukaryotic cells, which regulates numerous distinct cellular processes. This is achieved by the interaction of die catalytic subunit of PP1 (PP1C) with a diverse range of targeting subunits that localise PP1 C to specific sites within the cell, modulate its activity towards particular substrates and allow its activity to respond to extracellular signals.

The family of proteins that target PP1 to glycogen and regulate its activity towards the enzymes of glycogen metabolism consists of four members, $G_M$/PPP1R3, $G_L$/PPP1R4, PPP1R5 and PPP1R6/PTG. The liver specific glycogen-targeting subunit, $G_L$ is a 33 kDa protein that, when bound to PP1, enhances the rate at which the latter dephosphorylates and activates the rate determining enzyme in glycogen synthesis, glycogen synthase, whilst suppressing the rate at which it inactivates glycogen phosphorylase. The stimulation of hepatic glycogenolysis by glucagon (acting via cyclic AMP and PKA (Protein Kinase A)) and α-adrenergic agonsists (acting via $Ca^{2+}$) is achieved by activation of phosphorylase kinase, which increases the levels of the active phosphorylated form of glycogen phosphorylase (phosphorylase a). In addition, phosphorylase a binds to $G_L$ and potently inhibits its glycogen synthase phosphatase activity thereby inhibiting glycogen synthesis. Insulin lowers hepatic cAMP levels, causing a reduction in the level of phosphorylase a and alleviation of the phosphorylase a-mediated inhibition of the $PP1G_L$ complex, while the binding of glucose to phosphorylase a, increases the rate at which phosphorylase is inactivated. These mechanisms contribute to the stimulation of glycogen synthesis by insulin and high blood glucose. The inhibition of the $PP1G_L$ complex by phosphorylase a occurs at nanomolar concentrations and is thought to be via an allosteric mechanism since the $K_m$ for phosphorylase a as a substrate is in the micromolar range. This view is strengthened by the finding that phosphorylase a (but not phosphorylase b) binds directly to $G_L$ in protein blotting experiments.

Recent studies identified conserved regions between the glycogen targeting subunits $G_M$/PPP1R3 and $G_L$/PPP1R4. A peptide corresponding to one of these regions. $G_M$ 63–75 (amino acids 63 to 75 of $G_M$) was shown to bind PP1 and the amino terminal 38 residues of the myofibrillar targeting subunit of PP1 were also demonstrated to interact with PP1. The $G_M$ 63–75 peptide, which contains a small motif common to the myofibrillar binding subunit and many other of the PP1 targeting subunits has been crystallised as a complex with PP1 and its structure solved to 2.8 Å resolution. This motif, Lys/Arg-Val/Ile-Xaa-Phe/Trp, which has also been identified by a random peptide library approach, is found in all the four glycogen targeting subunit and is located at residues 60–64 of $G_L$. However, incubation of the $PP1G_L$ complex purified from hepatic glycogen-protein particles with a PP1-binding peptide from $G_M$ failed to dissociate the PP1-$G_L$ complex, even though the peptide abolished the suppression of phosphorylase phosphatase activity conferred on PP1 by association with $G_L$.

The present invention seeks to provide biological materials and methods which may be useful in the treatment of disorders, especially those such as diabetes type I and type II, associated with higher than normal levels of blood glucose.

According to a first aspect of the invention there is provided the use in medicine of a compound which is capable of blocking the interaction of phosphorylase a with the glycogen-targeting subunit ($G_L$) of protein phosphatase 1.

Preferably, the compound is for use in the manufacture of a medicament for use in treating disorders associated with higher than normal levels of blood glucose. Preferably the medicament is for use in the treatment of a disorder selected from type I and/or type II diabetes.

Preferably, the compound is a polypeptide comprising the sequence of the C-terminal 16 amino acids of human $G_L$ sequence, or a fragment or variant thereof of which is capable of binding phosphorylase a.

Thus, the sequence may be PEWPSYLGYEKLGPYY (SEQ ID. NO: 1), which may be the sequence of the C-terminal 16 amino acids of rat liver $G_L$.

By "variant" we include the meaning of polypeptides comprising an amino acid sequence which, although not identical to the 16 amino acid sequence, are capable of binding phosphorylase a.

By "fragment" we include the meaning that the polypeptide comprises less than the 16 amino acid sequence mentioned above, but is capable of binding phosphorylase a.

The identification of variants and fragments within the scope of the invention can be carried out using the methods described herein.

Preferably the polypeptide increases the activity of hepatic glycogen synthase.

Polypeptides in which one or more of the amino acid residues are chemically modified, before or after the polypeptide peptide is synthesised, may be used in accordance with the invention, providing that the function of the peptide, namely the blocking of the interaction between $G_L$ and phosphorylase a, remains substantially unchanged. Such modifications include forming salts which acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism.

The peptides may be present as single copies or as multiples, for example tandem repeats. Such tandem or multiple repeats may increase the activity of the polypeptide in blocking the binding of $G_L$ and phosphorylase a.

In a second aspect, the invention provides a pharmaceutical composition comprising an inhibitor compound which is capable of blocking the interaction of phosphorylase a with the glycogen targeting subunit ($G_L$) of protein phosphatase (PP1), together with a pharmaceutically acceptable excipient or carrier. Preferably the inhibitor compound comprises a polypeptide having the sequence of the C-terminal 16 amino acids of human $G_L$ sequence, or a fragment or variant thereof of which is capable of binding phosphorylase a, for example the 16 amino acid sequence PEWPSYLGYEKLGPYY (SEQ ID. NO: 1) or a fragment or variant thereof of which is capable of binding phosphorylase a.

In a third aspect, the invention provides a method of identifying an inhibitor compound that is capable of blocking the interaction of phosphorylase a with the glycogen-targeting subunit of PP1 comprising: providing a polypeptide comprising the sequence of the C-terminal 16 amino acids of human $G_L$ sequence, or a fragment or variant thereof of which is capable of binding phosphorylase a, for example the 16 amino acid sequence PEWPSYLGYEKLGPYY (SEQ ID. NO: 1), or a fragment or variant thereof which binds phosphorylase a; providing a test compound; and comparing the binding of the polypeptide by phosphorylase a in the presence or absence of the test compound; an inhibitor compound being identified by reduced binding in the presence of the test compound.

The inhibitor compound may be a drug-like compound or lead compound for the development of a drug-like compound. Thus, the method may be a method for identifying a drug-like compound or lead compound for the development of a drug-like compound that is capable of blocking the interaction of phosphorylase a with the glycogen-targeting subunit of PP1.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons molecular weight and which may be water-soluble. A drug-like compound may additionally exhibit features of selective interaction with a particular protein or proteins and be bioavailable and/or able to penetrate target cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

The compounds identified in the method may themselves be useful as a drug or they may represent lead compounds for the design and synthesis of more efficacious compounds.

The inhibitor compound may be an antibody or immunoglobulin-type molecule or a fragment thereof, as well known to those skilled in the art. An antibody or immunoglobulin-type molecule or a fragment thereof that cross-reacts/binds with a polypeptide having the sequence of the C-terminal 16 amino acids of human $G_L$ sequence, or a fragment or variant thereof of which is capable of binding phosphorylase a, for example the 16 amino acid sequence PEWPSYLGYEKLGPYY (SEQ ID. NO: 1) or a fragment or variant thereof of which is capable of binding phospho-rylase a may be such an inhibitor compound. An antibody or immunoglobulin-type molecule or a fragment thereof that cross-reacts/binds to $G_L$ may also be such an inhibitor compound. Such antibodies or immunoglobulin-type molecules or fragments thereof may be prepared by methods well known to those skilled in the art.

It will he appreciated that by "phosphorylase a" is included variants, fragments and fusions of phosphorylase a that have interactions or activities which are substantially the same as those of phosphorylase a with $G_L$ but which may be more convenient to use in an assay. For example, a fusion of phosphorylase a may be useful since said fusion may contain a moiety which may allow the fusion to be purified readily. It is preferred that the phosphorylase a is phosphorylase a from rabbit skeletal muscle. Phosphorylase a may be obtained from Sigma, Sgima-Aldrich Company Ltd, Fancy Road, Poole, Dorset, BH12 4QH.

Preferably, the phosphorylase a is labelled and the binding of phosphorylase a to the polypeptide is determined by measuring the amount of label quantitatively or qualitatively.

Conveniently, the phosphorylase a is labelled with a label selected from digoxigenin, $^{33}$P and $^{32}$P. Phosphorylase a labelled with $^{32}$P or $^{33}$P may be obtained by phosphorylation by phosphorylase kinase, as described in Cohen et al (1988) *Meth Enzymol* 159, 399–408. Phosphorylase kinase may be obtained from Sigma.

The disruption of the interaction between the said polypeptide and phosphorylase a can be measured in vitro using methods well known in the art of biochemistry and include any methods which can be used to assess protein-protein interactions.

The said interaction can also be measured within a cell, for example using the yeast two hybrid system as is well known in the art.

It will be appreciated that screening assays which are capable of high throughput operation will be particularly preferred. Examples may include cell based assays and protein-protein binding assays. An SPA-based (Scintillation Proximity Assay; Amersham International) system may be used. For example, beads comprising scintillant and the polypeptide having the sequence of the C-terminal 16 amino acids of human $G_L$ sequence, or a fragment or variant thereof of which is capable of binding phosphorylase a, for example the 16 amino acid sequence PEWPSYLGYEKLGPYY (SEQ ID. NO: 1) or a fragment or variant thereof of which is capable of binding phosphorylase a may be prepared. The beads may be mixed with a sample comprising $^{32}$P- or $^{33}$P-labelled phosphorylase a and with the test compound. Conveniently this is done in a 96-well format. The plate is then counted using a suitable scintillation counter, using known parameters for $^{32}$P SPA assays. Only $^{32}$P that is in proximity to the scintillant, i.e. only that bound to the polypeptide, is detected. Variants of such an assay, for example in which the polypeptide is immobilised on the scintillant beads via binding to an antibody, may also be used.

Other methods of detecting polypeptide/polypeptide interactions include ultrafiltration with ion spray mass spectroscopy/HPLC methods or other physical and analytical methods. Fluorescence Energy Resonance Transfer (FRET) methods, for example, well known to those skilled in the art, may be used, in which binding of two fluorescent labelled entities may be measured by measuring the interaction of the fluorescent labels when in close proximity to each other.

In a fourth aspect, the invention provides a compound which is identifiable by the methods according to the third aspect of the invention.

In a fifth aspect, the invention provides a method of reducing the blood glucose level of a mammalian animal comprising administering a therapeutically effective amount of an inhibitor compound as defined in accordance with the previous aspects of the invention. Preferably the mammalian animal is a human.

By "therapeutically effective amount" we include the meaning that enough of the compound is administered to produce a beneficial effect in the recipient, for example a beneficial decrease in hyperglycaemia.

A sixth aspect of the invention provides a method of identifying a compound which mimics the effect of phosphorylase a on $G_L$, the method comprising contacting said compound with $G_L$ and determining whether, in the presence of the compound, $G_L$ adopts the properties of $G_L$ in the presence of phosphorylase a.

By "mimics the effect of phosphorylase a" we include the meaning that the compound modifies a property of $G_L$ in such a way that $G_L$ acts, in at least one respect, like $G_L$ that is interacting with phosphorylase a.

It will be appreciated that the $G_L$ may be bound to PP1c, ie may be in the form of $PP1G_L$ and that the effect of the compound may be assessed by measuring the activity of $PP1G_L$, as well known to those skilled in the art, for example as described in WO97/37224 and references therein. Thus, the dephosphorylation of glycogen synthase by $PP1G_L$ may be measured. Thus a compound may be selected that decreases the activity of $PP1G_L$. It will be appreciated that the method may include the conduct of a screen or screens to determine that the compound interacts with the $G_L$ subunit and not with the PP1c subunit.

The said compound may be a drug-like compound or lead compound for the development of a drug-like compound. Thus, the method may be a method for identifying a drug-like compound or lead compound for the development of a drug-like compound that is capable of mimicking the effect of phosphorylase a on $G_L$ (a mimic compound).

In a seventh aspect, the invention provides a compound which is identifiable by the methods according to the sixth aspect of the invention.

In an eighth aspect, the invention provides a method of increasing the blood glucose level of a mammalian animal comprising administering a therapeutically effective amount of an inhibitor compound as defined in accordance with the previous aspects of the invention. Preferably the mammalian animal is a human. The mammalian animal, for example human, may have hypoglycaemia.

By "therapeutically effective amount" we include the meaning that enough of the compound is administered to produce a beneficial effect in the recipient, for example a beneficial decrease in hypoglycaemia.

A further aspect of the invention provides a kit of parts useful in carrying out the method of the third aspect of the invention. Thus such a kit may comprise phosphorylase a and a polypeptide comprising the sequence of the C-terminal 16 amino acids of human $G_L$ sequence, or a fragment or variant thereof of which is capable of binding phosphorylase a, for example the 16 amino acid sequence PEWP-SYLGYEKLGPYY (SEQ ID. NO: 1), or a fragment or variant thereof which binds phosphorylase a.

Preferred embodiments of the invention will now be described by way of example, with reference to the accompanying figures.

FIG. 1. Schematic representation of the $G_L$ and truncated forms generated by PCR (Polymerase Chain Reaction) or restriction digestion. The ability of $G_L$ and the $G_L$ fragments to bind PP1, glycogen and phosphorylase a is indicated. + indicates that binding was observed; − denotes that binding was tested but not detected; a indicates that aggregation of $G_L$ and its derivatives precluded testing of glycogen binding; interactions that were not tested are left blank.

FIG. 2. Identification of the $G_L$ region required for interaction with glycogen. GST(Glutathione-S-transferase)-$G_L$ fusion proteins containing truncated $G_L$ coding regions were examined for their ability to co-sediment with glycogen as described hereinafter. The supernatant (S) and the pellett (P) fractions obtained in the absence and presence of glycogen were subjected to SDS/PAGE (sodium dodecyl sulphate/polyacrylamide electrophoresis) on 12.5% polyacrylamide gels, transferred to nitrocellulose membranes and immunoblotted with affinity purified anti-$G_L$ protein antibodies. The position of the standard marker proteins, glycogen phosphorylase (97 kDa), bovine serum albumin (66 kDa), ovalbumin (43 kDa), and carbonic anhydrase (30 kDa) are indicated.

FIG. 4. Identification of the region binding PP1 in $G_L$. GST-$G_L$ (1–284) and GST-fusions containing truncated $G_L$ coding regions (2 μg) were separated on 12.5% SDS-polyacrylamide gels and either (A) stained with Coomassie blue or (B) transferred to nitrocellulose and probed with Digoxygenin-labelled PP1γ. The standard marker proteins are as in FIG. 2.

Phosphorylase a binds to the carboxyterminal terminal 16 amino acids of $G_L$. The relevant amino acid positions in $G_L$ are indicated above.

MATERIALS AND METHODS

1. Production of Glutathione S-transferase-$G_L$ Fusion Proteins

Figure 1:
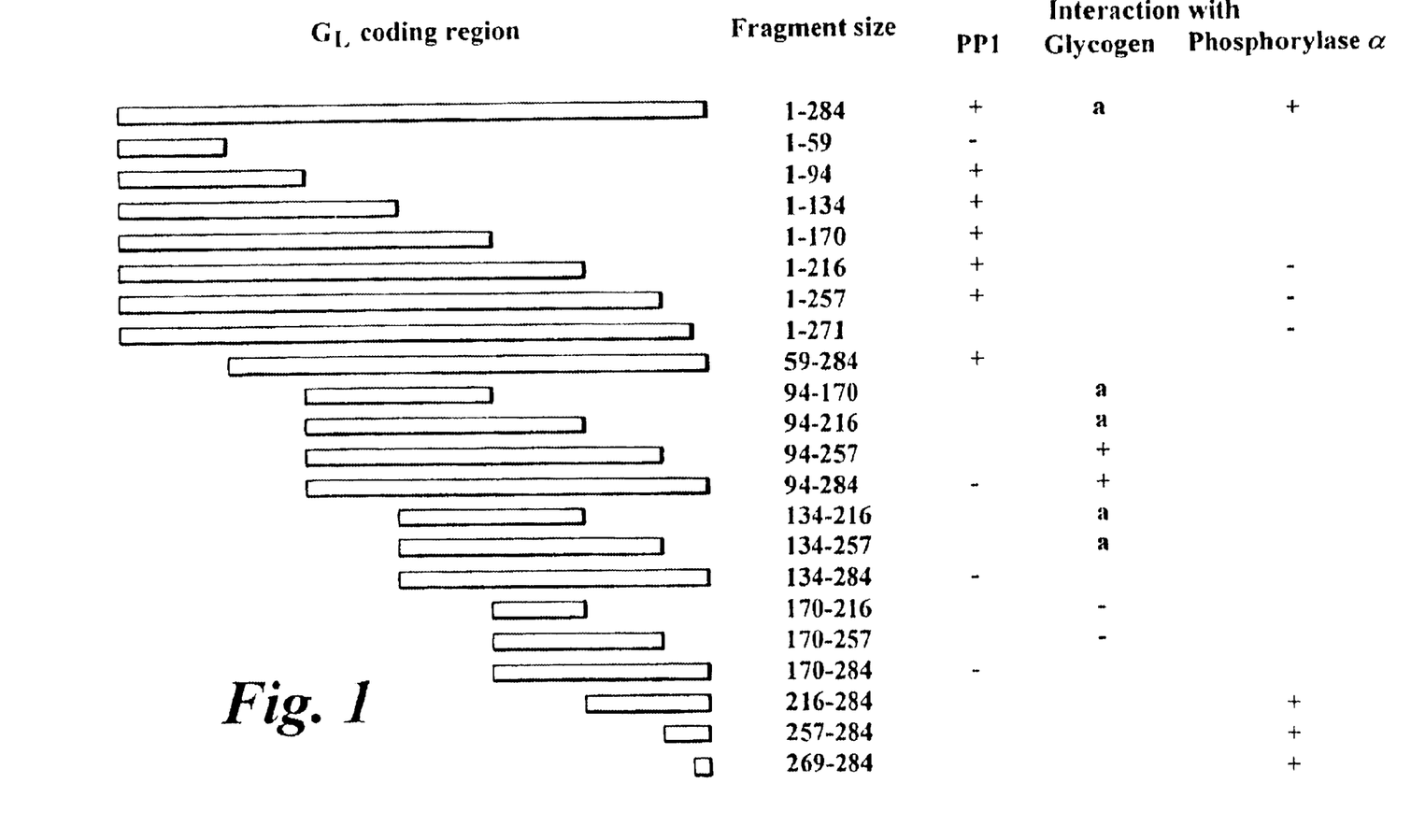

The pGEX-$G_L$ construct containing the complete coding region of $G_L$ was used as a template in polymerase chain reactions using primer pairs to generate a variety of $G_L$ coding region fragments (FIG. 1). The 5' coding primers all contained an NdeI site and the 3' reverse primers contained the termination codon and a XhoI site. The PCR products were then subcloned into the TOPO 2.1 PCR cloning vector (Invitrogen, Leek, The Netherlands) and verified by sequencing on an Applied Biosystems 373A automated DNA sequencer using Taq dye terminator cycle sequencing. The $G_L$ coding region fragments were subsequently excised by restriction cleavage with NdeI and XhoI and ligated into the pGEX-AH vector digested with the same restriction enzymes. The $G_L$ 1–94 and 1-170 truncations were generated by excision of a SacI-SacI and a HindIII-HindIII restriction fragment respectively from the pGEX-$G_L$ construct followed by religation of the plasmid. The $G_L$ 94–170 truncation was generated by NdeI-HindIII digestion of pGEX-$G_L$ 94–257 followed by ligation of the fragment into pGEX-AH vector digested with the same enzymes. Site directed mutation of the single mutants N152A, K157A, the double mutant N152A+K157A and the triple mutant K149A+N152A+L153A were generated using pGEX-$G_L$ 94–257 as template. The resultant constructs encoded glutathione S-transferase (GST) fused to $G_L$ coding region fragments of various lengths. Soluble GST-$G_L$ fusion-proteins were obtained by growing E. coli, transformed with the various pGEX-$G_L$ deletion constructs, in LB medium containing 100 μg/ml ampicillin and inducing expression in log phase growth at an $A_{600}$ nm of 0.5 with 0.2 mM isopropyl-thio-β-D-galactopyranoside. After 16 hours further growth at 26° C.–28° C., the E. coli were harvested and soluble GST-$G_L$ fusion proteins were purified in glutathione agarose.

2. Interaction of GST-$G_L$ Fusion Proteins with Digoxigenin-PP1γ and Phosphorylase a GST-$G_L$ fusion proteins were separated on SDS-PAGE and transferred to nitrocellulose membranes. They were probed with digoxigenin-PP1γ. Alternatively they were examined for binding of $^{32}$P-labelled phosphorylase a. Non-specific binding to the membranes was blocked by incubation in 5% (w/v) marvel dried milk powder, 25 mM Tris/HCl pH 7.5, 500 mM NaCl for 16 hours. The samples were then probed for 3 h with $^{32}$P-labelled phosphorylase a (100 nM) in 25 mM Tris/HCl pH 7.5, 250 mM NaCl, 1 mg/ml bovine serum albumin. The membranes were subsequently washed (3×30 min) with 25 mM Tris/HCl pH 7.5 before autoradiography.

3. Co-sedimentation of GST-$G_L$ Fusion Proteins with Hepatic Glycogen

Protein free glycogen was prepared by the following protocol. Glycogen-protein particles were isolated from the livers of New Zealand White rabbits. Protein was then stripped from the glycogen by boiling for 5 min in 1% (w/v) sodium dodecyl sulphate (SDS). The suspension was cooled to room temperature and centrifuged for 60 min at 100,000× g. The 100,000×g pellet was then resuspended in water, and the centrifugation and resuspension procedure repeated a further two times in order to completely remove residual SDS and protein. Any contaminating nucleotides were removed by incubating the glycogen for 15 min with mixed bed resin, AG 501-X8(D). The resin was removed by filtration and the glycogen concentration determined by the phenol/sulphuric acid method.

Protein free glycogen (10 mg/ml) in 50 mM Tris/HCl pH 7.5, 150 mM NaCl, 0.1% (v/v) 2-mercaptoethanol, 0.02% (w/v) Brij-35, 0.1 mg/ml bovine serum albumin was mixed with GST-$G_L$ fusion proteins (50 nM). After incubation on ice for 30 min, the samples were centrifuged for 90 min at 100,000×g. The supernatant and pellet fractions were denatured in SDS, subjected to SDS-polyacrylamide gel electrophoresis and transferred to nitrocellulose. The membranes were incubated overnight in 25 mM Tris/HCl pH 7.5, 250 mM NaCl, 0.1 % (w/v) Tween-20, 10% dried milk powder before probing with affinity purified sheep anti-$G_L$ protein antibodies (100 ng/ml in 25 mM Tris/HCl pH 7.5, 250 mM NaCl, 0.1% (w/v) Tween-20, 3% (w/v) dried milk powder), followed by several washes in the same buffer (without the dried milk powder) and incubation with horse radish peroxidase-conjugated anti-sheep antibodies (Pierce, UK). Immunoreactive bands were visualised using the enhanced chemiluminescence system (Amersham International, Bucks, UK.)

4. Results 4.1 Residues 94–25 7 of $G_L$ are Required for Binding to Glycogen

Figure 2:
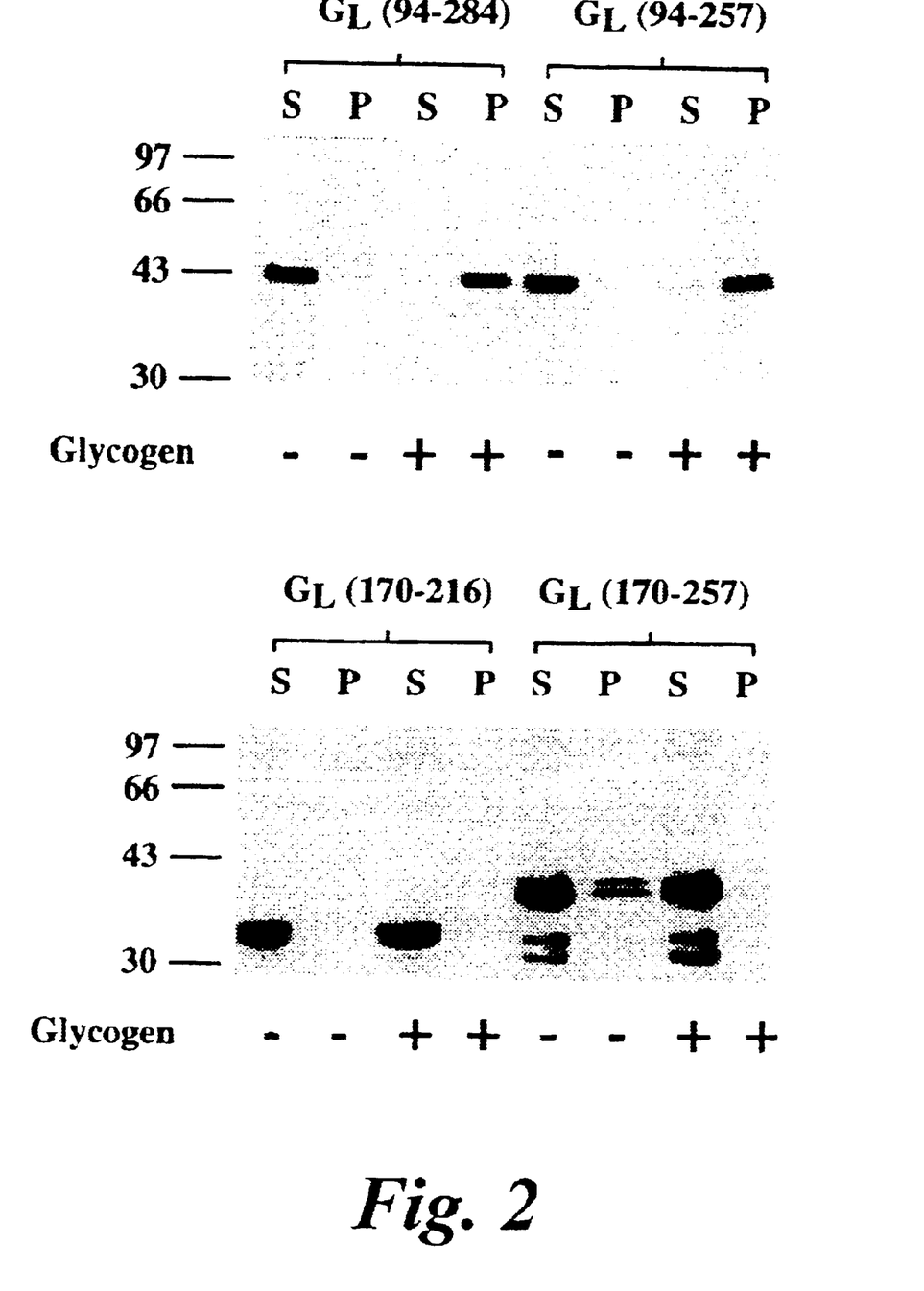

GST-$G_L$, containing the full-length $G_L$ coding region, and several of the GST-$G_L$ truncations {GST-$G_L$(94–216), GST-$G_L$(94–170), GST-$G_L$(134–170), GST-$G_L$(134–216), GST-$G_L$(134–257)} exhibited a strong tendency to aggregate and were pelleted at 100 000×g for 1 h, even in the absence of glycogen. Therefore these constructs could not be tested for glycogen dependent sedimentation. Of the GST-fusion proteins that did not aggregate, GSTG$_L$(94–284) and GSTG$_L$(94–257) were both detected exclusively in the 100,000×g pellet obtained by centrifugation in the presence of glycogen (FIG. 2). In contrast GST-$G_L$(170–216) and GST-$G_L$(170–257) did not bind to glycogen, being detected exclusively in the 100,000×g supernatant fraction in the presence of glycogen (FIG. 2). GST-$G_L$(94–257) carrying the single mutations N152A or K157A, the double mutation N152A+K157A, or the triple mutation K149A+N152A+L153A were all found to sediment in the presence of glycogen (data not shown).

Figure 3:
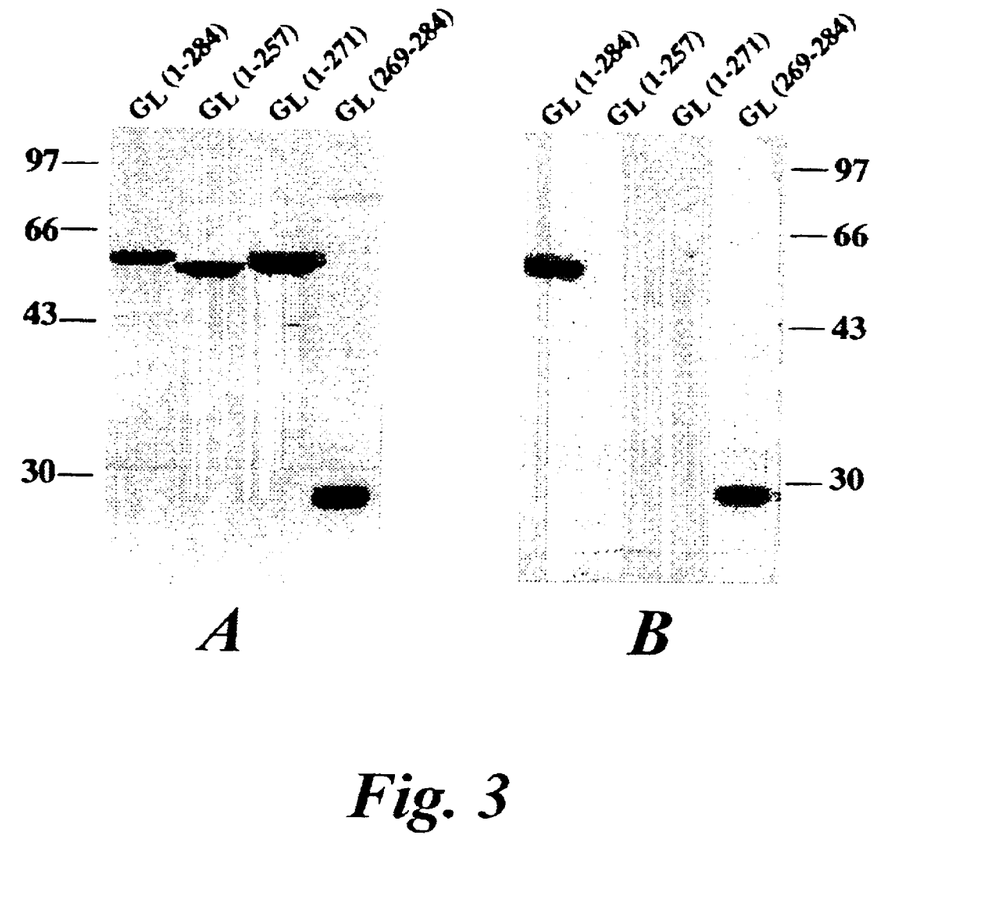
FIG. 3. Identification of the binding site for phosphorylase a lies in the 16 caboxy-terminal amino acids of $G_L$. GST-$G_L$ (1–284) and GST-fusions containing truncated $G_L$ coding regions (2 μg) were separated on 12.5% SDS-polyacrylamide gels and either (A) stained with Coomassie blue or (B) transferred to nitrocellulose and probed with 100 nM $^{32}$P-labelled phosphorylase a. The standard marker proteins are as in FIG. 2.

4.2 The phosphorylase a Binding Site Lies in the C-terminal 16 Amino Acids of $G_L$ In order to identify the region of $G_L$ that is responsible for the binding of phosphorylase a, GST-$G_L$ and its truncated forms were transferred to nitrocellulose membranes and tested for their ability to bind $^{32}$P-phosphorylase a. $^{32}$P-labelled phosphorylase a was found to bind to GST-$G_L$ containing the entire $G_L$ coding region and to GST-$G_L$(216–284), GST-$G_L$(257–284) and GST-$G_L$(269–284) but not to GST-$G_L$(1–216), GST-$G_L$(1–257) and GST-$G_L$(1–271) {FIG. 3 and data not shown). These results indicate that the phosphorylase a binding domain lies in the carboxy-terminal 16 amino acids of $G_L$.

4.3 The PPI-binding Domain Lies between Residues 59 and 94 of $G_L$

Figure 4:
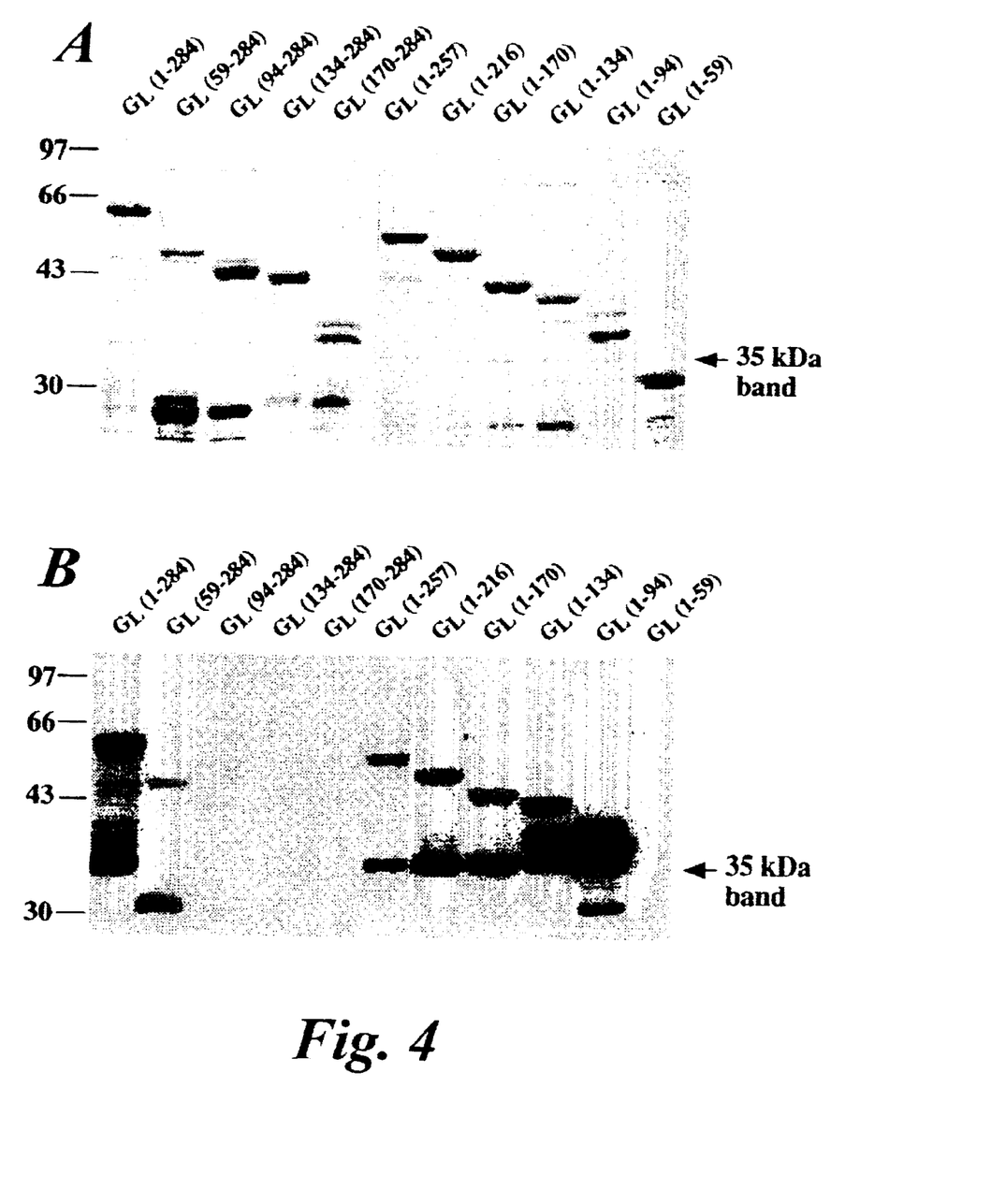

The GST-$G_L$ truncations were also tested for their ability to bind digoxigenin-labelled PP1γ after transfer to nitrocellulose membranes. FIG. 4 shows that digoxigenin-PPI binds to GST-$G_L$(1–284), GST-$G_L$(1–94) and GST-$G_L$(59–284) but not to GST-$G_L$(1–59) or GST-$G_L$(94–284), GST-$G_L$(134–284) or GST-$G_L$(170–284). From these interactions, the principal PP1 binding domain must lie between residues 59 and 94 of $G_L$. Several proteolytically degraded fragments present in the preparations were also recognised by digoxygenin-PP1, in particular a minor 35 kDa Coomassie-blue staining band that migrated slightly faster than GST-$G_L$(1–94) but slower than GST-$G_L$(1–59). Since this proteolytic fragment was retained on glutathione-Sepharose, it is likely to comprise GST linked to the first 75–80 residues of $G_L$. The strong signal with digoxigenin-PP1 may be explained by a more effective renaturation of this fragment from SDS on the nitrocellulose membrane.

5. Discussion

Figure 5:
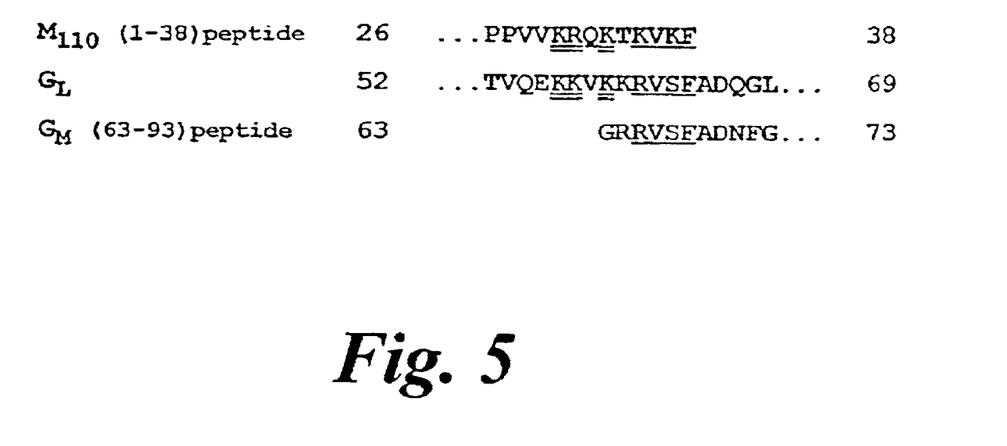
FIG. 5. Comparison of the sequences of rat $M_{110}$ 1–38 peptide and rabbit $G_M$ 63–93 peptide with $G_L$ in the region of the RVSF motif (underlined). Three basic residues (Lys or Arg)* preceding the RVSF motif that are conserved in $M_{110}$ and $G_L$ but not present in the $G_M$ 63–93 peptide are double underlined. No other clear sequence similarities between $M_{110}$ 1–38 peptide and $G_L$ were apparent in the region preceding that shown.
Figure 6:
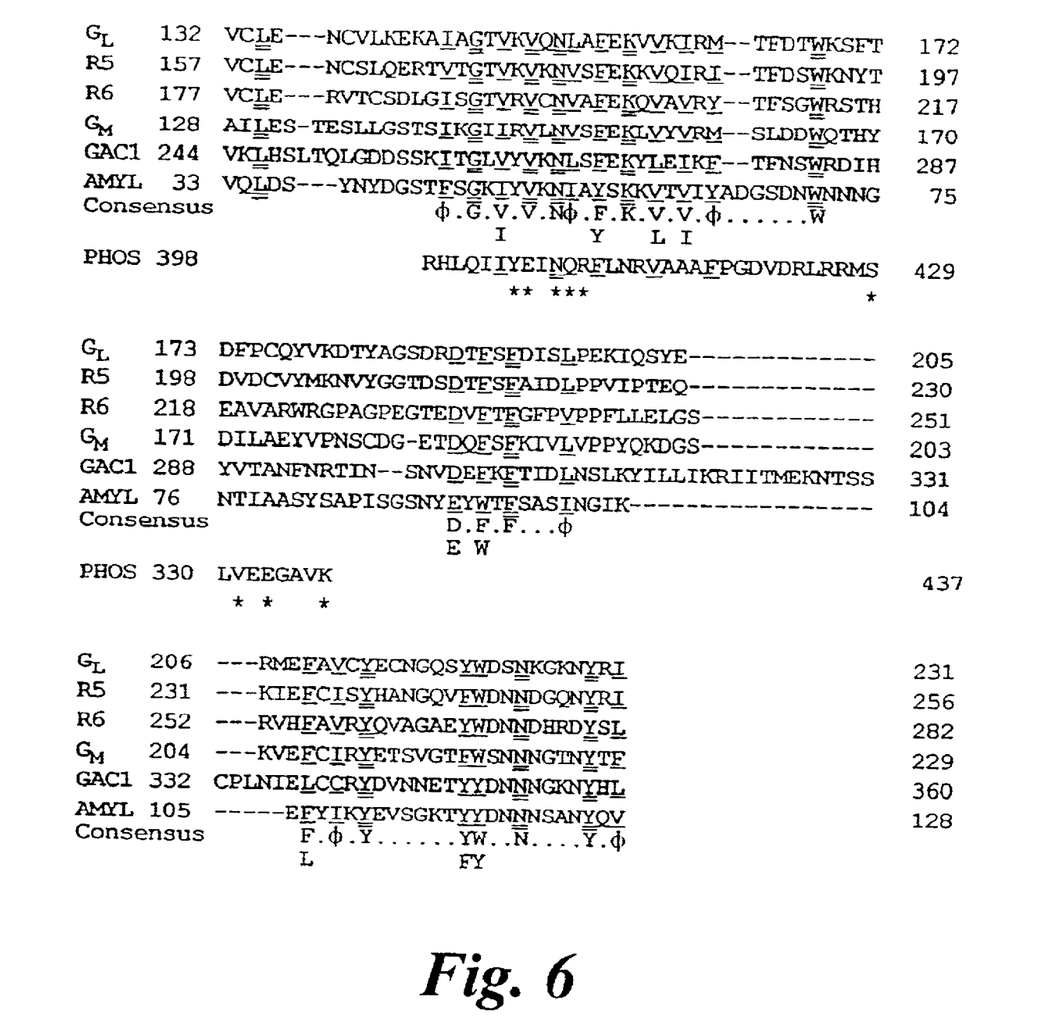
FIG. 6. Comparison of the polysaccharide binding domain of the mammalian glycogen targeting subunits, *S. cerevisiae* GAC1, *Rhizopus oryzae* glucoamylase (AMYL) with phosphorylase (PHOS) glycogen binding (storage) site. The sequences are rat $G_L$, human PPP1R5, human PPP1R6, human $G_M$, *S. cerevisiae* GAC1, *R. oryzae* glucoamylase and rabbit skeletal muscle glycogen phosphorylase. A consensus sequence for the polysaccharide binding domain of the glycogen targeting subunits and glucoamylase is shown. Conserved residues are underlined and identical residues are double underlined. The maltohepatose binding residues in phosphorylase are marked with an asterisk.

Here we have identified three distinct functional domains on the rat liver glycogen-targeting subunit of protein phosphatase 1. The section comprising amino acids 59–94 is both necessary and sufficient for binding to PP1. This region contains the sequence, Arg-Val-Ser-Phe (SEQ ID. NO: 2) which conforms to the consensus PP1-binding motif determined for other PP1-binding subunits. The data provides further evidence for the importance of this short motif in the binding of PP1 to its targeting subunits. The results also indicate that no other domains outside of residues 59–94 can initiate and maintain an interaction with PP1 independently of the RVSF motif. Previous experiments demonstrated that a peptide comprising the amino terminal 38 residues of the $M_{110}$ subunit of the myosin targeting subunit of PP1 ($M_{110}$ 1–38) could disrupt the PP1$G_L$ complex, while a peptide comprising residues 63–93 of the skeletal muscle glycogen targeting subunit ($G_M$ 63–93) did not abolish binding of $G_L$ to PP1. This data suggests that secondary sites of PP1$G_L$ interaction are likely to involve residues that are identical in $M_{110}$ 1–38 and $G_L$ but distinct (or not included) in $G_M$ 63–93. A comparison of the sequences of $M_{110}$ 1–38 peptide and $G_M$ 63–93 peptide with $G_L$ in the region of the RVSF motif identifies 3 basic residues (Lys or Arg) preceding the RVSF motif that are identical in $M_{110}$ and $G_L$ but are not present in the $G_M$ 63–93 peptide (FIG. 5). The basic residues in positions –2, –4 and –5 with respect to the RVSF motif may therefore provide the secondary interactions of $G_L$ with PP1 that are not disrupted by the $G_M$ 63–93 peptide. The crystal structure of PP1 complexed to the $G_M$ 63–75 peptide reveals the presence of an acidic domain in PP1, that ties to the amino terminal end of the RVSF motif in the bound peptide and thus has the potential to interact with the basic residues in $G_L$ and tie $M_{110}$ peptide. The sequence similarity noted previously between the mammalian glycogen targeting subunits and glucoamylase from *Rhizopus oryzae*, which binds starch, spans a region comprising amino acids 134–231 of $G_L$[5,6] and (FIG. 6). This present study demonstrates that the region 94–257 of $G_L$ is capable of binding to glycogen, while the truncated GST fusion proteins GST-$G_L$(170–216) or GST-$G_L$(170–257) fail to bind to glycogen. The interaction of GST-$G_L$(94–170) or GST-$G_L$(134–170) with glycogen could not be tested due to the aggregation of this fragment. However, residues 148–168 of $G_L$ show some sequence similarities (FIG. 6) to the region in phosphorylase identified in crystallographic studies to bind to maltoheptaose and believed to bind to glycogen in vivo. The crystal structure of phosphorylase shows that the side chains of conserved hydrophobic amino acids in this section point inwards and appear to be involved in maintaining the orientation of the α-helix that binds maltoheptaose. Of the residues shown to bind to maltoheptaose, only the Asn corresponding to Asn152 in $G_L$ is identical in the glycogen targeting subunits and phosphorylase. However, mutation of N152A in GST-$G_L$(94–257) did not prevent this fragment binding to glycogen, nor did the double mutation of K157A+N152A. The triple mutation K149A+N152A+L153A of residues which are conserved in the glycogen targeting subunits and are aligned with those binding maltoheptaose in phosphorylase (FIG. 6) also did not prevent the binding of GST-$G_L$(94–257) to glycogen. The results suggest that all of the conserved sections in $G_L$ (134–231) are likely to be required for binding to glycogen either by making direct contact with glycogen or by contributing to structural elements required for this binding. They further indicate that the binding site of the PP1 glycogen targeting subunit and glucoamylase to polysaccharides is distinct from the glycogen binding (storage) site of phosphorylase.

Figure 7:
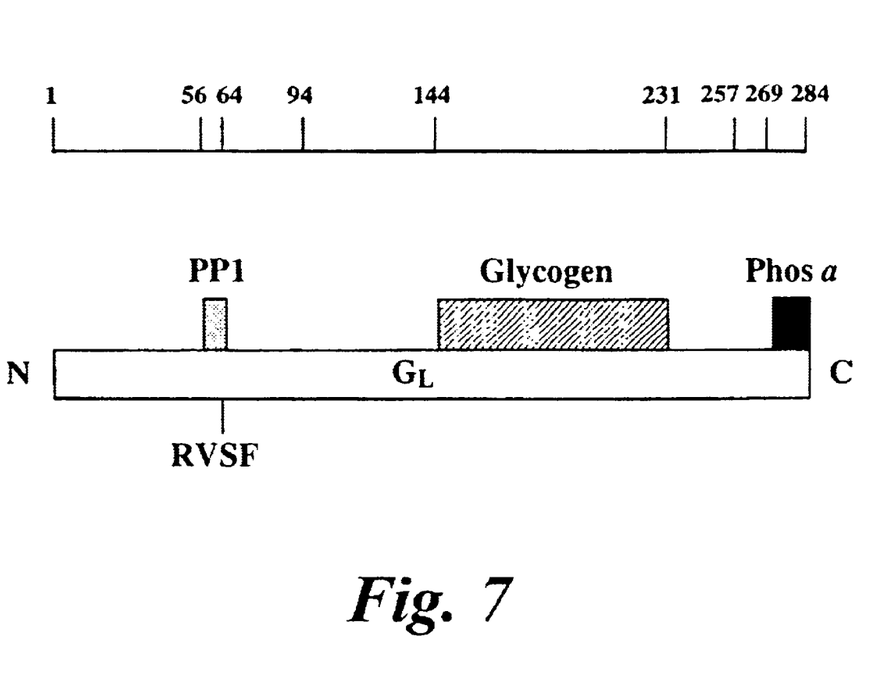
FIG. 7. Schematic representation of the domains in $G_L$ that interact with PP1, glycogen and phosphorylase a. PP1 binds to the Arg-Val-Ser-Phe (SEQ ID. NO: 2) motif located at residues 61–64. The basic sequence preceding this motif is also likely to be involved in binding PP1. Residues 134–231 include the conserved residues among the glycogen subunits that lie in the 94–257 fragment of $G_L$ that co-sediments with glycogen.

The allosteric inhibition of the glycogen synthase phosphatase activity of PP1GL by phosphorylase a is mediated by the binding of phosphorylase a to $G_L$. The results presented here demonstrate that the 16 amino acids at the C-terminus of $G_L$ are essential for the interaction with phosphorylase a (FIG. 7). However, although this short region is sufficient for the binding of phosphorylase a, it is likely that other regions of $G_L$ are required to transmit the allosteric effect of this molecule to the active site of PP1. Nevertheless, the unexpected identification of a short sequence in $G_L$ as crucial for the binding of phosphorylase a and therefore also for inhibition of glycogen synthase phosphatase activity provides a rationale for searching for small molecules that might block this inhibition. Raising the level of glycogen synthase phosphatase and consequently glycogen synthase may be useful in disorders, such as diabetes, where hyperglycaemia is a severe problem.

The other three glycogen-binding subunits, $G_M$/PPP1R3, PPP1R5 and PPP1R6 do not show significant sequence similarity to the carboxy-terminus of $G_L$ which explains why $G_M$ is not inhibited by phosphorylase a and PPP1R5 and PPP1R6 have not been found to bind phosphorylase a after transfer to nitrocellulose membranes. PTG, the mouse homologue of the human glycogen-targeting subunit PPP1R5, has been reported to bind to phosphorylase a, as well as to several other regulatory enzymes of glycogen metabolism. If this is the case, then the amino acid sequence binding, phosphorylase a in PIG is significantly different from that in $G_L$.

6. Method of Identifying an Inhibitor Compound which is Capable of Blocking the Interaction of Phosphorylase a with the Glycogen-targeting Subunit of PP1.

GST-$G_L$ forms containing the 16 amino acid sequence produced in accordance with the previously described methods are transferred to nitrocellulose membranes and tested for their ability to bind $^{32}$P-labelled phosphorylase a in the presence and absence of a test compound. A decrease in the amount of $^{32}$P phosphorylase a binding in the presence of the test compound compared to the amount of binding in the absence of the test compound is indicative of an inhibitory compound of the invention.

A compound which is capable of blocking the phosphorylase a $G_L$ interaction should increase the activity of PP1-$G_L$ and consequently that of glycogen synthase, leading to the increased conversion of the glucose into glycogen. Hence, the compound should be an effective drug in lowering blood glucose by converting it into hepatic glycogen.

Previously, it was reasonable to assume that since phosphorylase a is a large molecule, it might bind to many sites or an extensive region of $G_L$. Consequently, the probability of finding a drug which could block this interaction was thought to be low. The unexpected identification of the binding site on $G_L$ has been only 16 amino acids long (or smaller) increases the likelihood of finding a drug that will prevent phosphorylase a inhibition of the PP1-$G_L$ complex and hence increase glycogen synthesis.

7. Use in Medicine

The aforementioned compounds of the invention or a formulation thereof may be administered by any conventional method including oral and parenteral (e.g. subcutaneous or intramuscular) injection. The treatment may consist of a single dose or a plurality of doses over a period of time.

8. Pharmaceutical Compositions of the Invention

The following examples illustrate pharmaceutical formulations according to the invention in which the active ingredient is a compound of the invention.

Example A: Tablet

| | |
|---|---|
| Active ingredient | 100 mg |
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

Example B: Tablet Formulations

The following formulations A and B are prepared by wet granulation of the ingredients with a solution of povidone, followed by addition of magnesium stearate and compression.

| | mg/tablet | mg/tablet |
|---|---|---|
| Formulation A | | |
| (a) Active ingredient | 250 | 250 |
| (b) Lactose B. P. | 210 | 26 |
| (c) Povidone B. P. | 15 | 9 |
| (d) Sodium Starch Glycolate | 20 | 12 |
| (e) Magnesium Stearate | 5 | 3 |
| | 500 | 300 |
| Formulation B | | |
| (a) Active ingredient | 250 | 250 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
| | 500 | 300 |
| Formulation C | | |
| Active ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients. The lactose used in formulation E is of the direction compression type.

| | mg/capsule |
|---|---|
| Formulation D | |
| Active Ingredient | 250 |
| Pregelatinised Starch NF15 | 150 |
| | 400 |
| Formulation E | |
| Active Ingredient | 250 |
| Lactose | 150 |

| | mg/capsule |
|---|---|
| Avicel ® | 100 |
| | 500 |

Formulation F (Controlled Release Formulations)

The formulation is prepared by wet granulation of the ingredients (below) with a solution of povidone followed by the addition of magnesium stearate and compression.

| | | mg/tablet |
|---|---|---|
| (a) | Active Ingredient | 500 |
| (b) | Hydroxypropylmethylcellulose (Methocel K4M Premium) ® | 112 |
| (c) | Lactose B. P. | 53 |
| (d) | Povidone B. P. C. | 28 |
| (e) | Magnesium Stearate | 7 |
| | | 700 |

Drug release takes place over a period of about 6–8 hours and was complete after 12 hours.

Example D: Capsule Formulations

Formulation A

A capsule formulation is prepared by admixing the ingredients of Formulation D in Example C above and filling into a two-part hard gelatin capsule. Formulation B (infra) is prepared in a similar manner.

| | mg/capsule |
|---|---|
| Formulation B | |
| (a) Active ingredient | 250 |
| (b) Lactose B. P. | 143 |
| (c) Sodium Starch Glycolate | 25 |
| (d) Magnesium Stearate | 2 |
| | 420 |
| Formulation C | |
| (a) Active ingredient | 250 |
| (b) Macrogol 4000 BP | 350 |
| | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

|  | mg/capsule |
|---|---|
| (a) Active ingredient | 250 |
| (b) Microcrystalline Cellulose | 125 |
| (c) Lactose BP | 125 |
| (d) Ethyl Cellulose | 13 |
|  | 513 |

Example E: Injectable Formulation

| Active ingredient | 0.200 g |
|---|---|

Sterile, pyrogen free phosphate buffer (pH7.0) to 10 ml

The active ingredient is dissolved in most of the phosphate buffer (35–40° C.), then made up to volume and filtered through a sterile micropore filter into a sterile 10 ml amber glass vial (type 1) and sealed with sterile closures and overseals.

Example F: Intramuscular injection

| Active ingredient | 0.20 g |
|---|---|
| Benzyl Alcohol | 0.10 g |
| Glucofurol 75 ® | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G: Syrup Suspension

| Active ingredient | 0.2500 g |
|---|---|
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H: Supppsitory

|  | mg/suppository |
|---|---|
| Active ingredient (63 µm)* | 250 |
| Hard Fat, BP (Witepsol H15 - Dynamit Nobel) | 1770 |
|  | 2020 |

*The active ingredient is used as a powder wherein at least 90% of the particles are of 63 µm diameter or less.

One fifth of the Witepsol H15 is melted in a steam-jacketed pan at 45° C. maximum. The active ingredient is sifted through a 200 µm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 µm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I: Pessaries

|  | mg/pessary |
|---|---|
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylnethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

Whilst it is possible for a compound of the invention to be administered alone, it is preferable to present it as a pharmaceutical formulation, together with one or more acceptable carriers. The carrier(s) must be []acceptable[]in the sense of being compatible with the compound of the invention and not deleterious to the recipients thereof. Typically, the carriers will be water or saline which will be sterile and pyrogen free.

What is claimed is:

1. A pharmaceutical composition comprising an inhibitor compound which is capable of blocking the interaction of phosphorylase a with the glycogen-targeting subunit ($G_L$) of protein phosphatase 1, together with a pharmaceutically acceptable excipient or carrier wherein the inhibitor compound comprises a polypeptide having SEQ ID. NO: 1 or a fragment thereof which is capable of binding phosphorylase a.

2. A pharmaceutical composition as claimed in claim 1 wherein the polypeptide consists of a fragment of the glycogen-targeting subunit of protein phosphatase 1 SEQ ID NO: 1.

3. A method of identifying an inhibitor compound which is capable of blocking the interaction of phosphorylase a with the glycogen-targeting subunit of protein phosphatase 1 comprising;
   providing a polypeptide comprising SEQ ID. NO: 1 or fragment thereof which binds phosphorylase a;
   providing a test compound; and
   comparing the binding of the polypeptide by phosphorylase a in the presence and absence of the test compound; an inhibitor being identified by reduced binding of the polypeptide in the presence of the test compound.

4. A method as claimed in claim 3 wherein
   the phosphorylase a is labelled;
   the polypeptide is immobilised on a support; and
   the binding of phosphorylase a to the polypeptide is determined by measuring the amount of label bound to the support.

5. A method as claimed in claim 4 wherein phosphorylase a is labelled with a label selected from digoxigenin, $^{32}$P or $^{33}$P.

6. A method of reducing the blood glucose level of a mammalian animal comprising administering a therapeutically effective amount of a compound which is capable of blocking the interaction of phosphorylase a with the glycogen-targeting subunit $G_L$ of protein phosphatase 1, wherein the compound comprises SEQ ID. NO: 1 or a fragment thereof which is capable of binding phosphorylase a.

7. A method as claimed in claim 6 wherein the mammalian animal is a human.

8. A method of blocking the interaction of phosphorylase a with the glycogen-targeting subunit ($G_L$) of protein phosphatase 1 comprising:
   contacting phosphorylase a with a compound in an amount effective to block the interaction of the phosphorylase a with the glycogen-targeting unit ($G_L$) of protein phosphatase 1 wherein the compound is a polypeptide comprising SEQ ID NO:1 or a fragment thereof which is capable of binding phosphorylase a.

9. The method according to claim 8, wherein the compound is administered to a subject having a disorder associated with higher than normal blood glucose levels.

10. The method according to claim 9 wherein the disorder is selected from type I or type II diabetes.

11. The method according to claim 8 wherein the polypeptide increases the activity of hepatic glycogen synthase.

12. A compound which is capable of blocking the interaction of phosphorylase a with the glycogen-targeting subunit ($G_L$) of protein phosphatase 1, wherein the compound comprises a polypeptide having SEQ ID. NO: 1 or a fragment thereof which is capable of binding phosphorylase a.

* * * * *

SEQUENCE LISTING

```
<160> NUMBER OF SEQ ID NOS: 12

<210> SEQ ID NO 1
<211> LENGTH: 16
<212> TYPE: PRT
<213> ORGANISM: Rattus sp.

<400> SEQUENCE: 1

Pro Glu Trp Pro Ser Tyr Leu Gly Tyr Glu Lys Leu Gly Pro Tyr Tyr
 1               5                  10                  15

<210> SEQ ID NO 2
<211> LENGTH: 4
<212> TYPE: PRT
<213> ORGANISM: Rattus sp.

<400> SEQUENCE: 2

Arg Val Ser Phe
 1

<210> SEQ ID NO 3
<211> LENGTH: 13
<212> TYPE: PRT
<213> ORGANISM: Rattus sp.

<400> SEQUENCE: 3

Pro Pro Val Val Lys Arg Gln Lys Thr Lys Val Lys Phe
 1               5                  10

<210> SEQ ID NO 4
<211> LENGTH: 18
<212> TYPE: PRT
<213> ORGANISM: Rattus sp.

<400> SEQUENCE: 4

Thr Val Gln Glu Lys Lys Val Lys Lys Arg Val Ser Phe Ala Asp Gln
 1               5                  10                  15

Gly Leu
```

```
<210> SEQ ID NO 5
<211> LENGTH: 11
<212> TYPE: PRT
<213> ORGANISM: Rabbit

<400> SEQUENCE: 5

Gly Arg Arg Val Ser Phe Ala Asp Asn Phe Gly
 1               5                  10

<210> SEQ ID NO 6
<211> LENGTH: 100
<212> TYPE: PRT
<213> ORGANISM: Rattus sp.

<400> SEQUENCE: 6

Val Cys Leu Glu Asn Cys Val Leu Lys Glu Lys Ala Ile Ala Gly Thr
 1               5                  10                  15

Val Lys Val Gln Asn Leu Ala Phe Glu Lys Val Val Lys Ile Arg Met
            20                  25                  30

Thr Phe Asp Thr Trp Lys Ser Phe Thr Asp Phe Pro Cys Gln Tyr Val
        35                  40                  45

Lys Asp Thr Tyr Ala Gly Ser Asp Arg Asp Thr Phe Ser Phe Asp Ile
    50                  55                  60

Ser Leu Pro Glu Lys Ile Gln Ser Tyr Glu Arg Met Glu Phe Ala Val
65                  70                  75                  80

Cys Tyr Glu Cys Asn Gly Gln Ser Tyr Trp Asp Ser Asn Lys Gly Lys
                85                  90                  95

Asn Tyr Arg Ile
            100

<210> SEQ ID NO 7
<211> LENGTH: 100
<212> TYPE: PRT
<213> ORGANISM: Homo sapiens

<400> SEQUENCE: 7

Val Cys Leu Glu Asn Cys Ser Leu Gln Glu Arg Thr Val Thr Gly Thr
 1               5                  10                  15

Val Lys Val Lys Asn Val Ser Phe Glu Lys Lys Val Gln Ile Arg Ile
            20                  25                  30

Thr Phe Asp Ser Trp Lys Asn Tyr Thr Asp Val Asp Cys Val Tyr Met
        35                  40                  45

Lys Asn Val Tyr Gly Gly Thr Asp Ser Asp Thr Phe Ser Phe Ala Ile
    50                  55                  60

Asp Leu Pro Pro Val Ile Pro Thr Glu Gln Lys Ile Glu Phe Cys Ile
65                  70                  75                  80

Ser Tyr His Ala Asn Gly Gln Val Phe Trp Asp Asn Asn Asp Gly Gln
                85                  90                  95

Asn Tyr Arg Ile
            100

<210> SEQ ID NO 8
<211> LENGTH: 101
<212> TYPE: PRT
<213> ORGANISM: Homo sapiens

<400> SEQUENCE: 8

Val Cys Leu Glu Arg Val Thr Cys Ser Asp Leu Gly Ile Ser Gly Thr
 1               5                  10                  15
```

-continued

Val Arg Val Cys Asn Val Ala Phe Glu Lys Gln Val Ala Val Arg Tyr
            20                  25                  30

Thr Phe Ser Gly Trp Arg Ser Thr His Glu Ala Val Ala Arg Trp Arg
        35                  40                  45

Gly Pro Ala Gly Pro Glu Gly Thr Glu Asp Val Phe Thr Phe Gly Phe
        50                  55                  60

Pro Val Pro Pro Phe Leu Leu Glu Leu Gly Ser Arg Val His Phe Ala
65                  70                  75                  80

Val Arg Tyr Gln Val Ala Gly Ala Glu Tyr Trp Asp Asn Asn Asp His
                85                  90                  95

Arg Asp Tyr Ser Leu
            100

<210> SEQ ID NO 9
<211> LENGTH: 102
<212> TYPE: PRT
<213> ORGANISM: Homo sapiens

<400> SEQUENCE: 9

Ala Ile Leu Glu Ser Thr Glu Ser Leu Leu Gly Ser Thr Ser Ile Lys
1               5                   10                  15

Gly Ile Ile Arg Val Leu Asn Val Ser Phe Glu Lys Leu Val Tyr Val
            20                  25                  30

Arg Met Ser Leu Asp Asp Trp Gln Thr His Tyr Asp Ile Leu Ala Glu
        35                  40                  45

Tyr Val Pro Asn Ser Cys Asp Gly Glu Thr Asp Gln Phe Ser Phe Lys
    50                  55                  60

Ile Val Leu Val Pro Pro Tyr Gln Lys Asp Gly Ser Lys Val Glu Phe
65                  70                  75                  80

Cys Ile Arg Tyr Glu Thr Ser Val Gly Thr Phe Trp Ser Asn Asn Asn
                85                  90                  95

Gly Thr Asn Tyr Thr Phe
            100

<210> SEQ ID NO 10
<211> LENGTH: 117
<212> TYPE: PRT
<213> ORGANISM: Saccharomyces cerevisiae

<400> SEQUENCE: 10

Val Lys Leu His Ser Leu Thr Gln Leu Gly Asp Asp Ser Ser Lys Ile
1               5                   10                  15

Thr Gly Leu Val Tyr Val Lys Asn Leu Ser Phe Glu Lys Tyr Leu Glu
            20                  25                  30

Ile Lys Phe Thr Phe Asn Ser Trp Arg Asp Ile His Tyr Val Thr Ala
        35                  40                  45

Asn Phe Asn Arg Thr Ile Asn Ser Asn Val Asp Glu Phe Lys Phe Thr
    50                  55                  60

Ile Asp Leu Asn Ser Leu Lys Tyr Ile Leu Ile Lys Arg Ile Ile
65                  70                  75                  80

Thr Met Glu Lys Asn Thr Ser Ser Cys Pro Leu Asn Ile Glu Leu Cys
                85                  90                  95

Cys Arg Tyr Asp Val Asn Asn Glu Thr Tyr Tyr Asp Asn Asn Asn Gly
            100                 105                 110

Lys Asn Tyr His Leu
            115

-continued

```
<210> SEQ ID NO 11
<211> LENGTH: 96
<212> TYPE: PRT
<213> ORGANISM: Rhizopus oryzae

<400> SEQUENCE: 11

Val Gln Leu Asp Ser Tyr Asn Tyr Asp Gly Ser Thr Phe Ser Gly Lys
 1               5                  10                  15

Ile Tyr Val Lys Asn Ile Ala Tyr Ser Lys Lys Val Thr Val Ile Tyr
            20                  25                  30

Ala Asp Gly Ser Asp Asn Trp Asn Asn Asn Gly Asn Thr Ile Ala Ala
        35                  40                  45

Ser Tyr Ser Ala Pro Ile Ser Gly Ser Asn Tyr Glu Tyr Trp Thr Phe
    50                  55                  60

Ser Ala Ser Ile Asn Gly Ile Lys Glu Phe Tyr Ile Lys Tyr Glu Val
65                  70                  75                  80

Ser Gly Lys Thr Tyr Tyr Asp Asn Asn Asn Ser Ala Asn Tyr Gln Val
                85                  90                  95

<210> SEQ ID NO 12
<211> LENGTH: 40
<212> TYPE: PRT
<213> ORGANISM: Rabbit

<400> SEQUENCE: 12

Arg His Leu Gln Ile Ile Tyr Glu Ile Asn Gln Arg Phe Leu Asn Arg
 1               5                  10                  15

Val Ala Ala Phe Pro Gly Asp Val Asp Arg Leu Arg Arg Met Ser
            20                  25                  30

Leu Val Glu Glu Gly Ala Cys Lys
            35                  40
```